United States Patent [19]

Carlsson et al.

[11] Patent Number: 4,586,925
[45] Date of Patent: May 6, 1986

[54] HOSE SET FOR EXTRACORPOREAL TREATMENT OF BLOOD AND SIMILAR LIQUIDS

[75] Inventors: Per-Olov A. V. Carlsson, Sosdala; Rolf E. Karlberg, Veberod, both of Sweden

[73] Assignee: Gambro Lundia AB, Sweden

[21] Appl. No.: 530,110

[22] Filed: Sep. 7, 1983

[30] Foreign Application Priority Data

Sep. 10, 1982 [SE] Sweden .................................. 8205160

[51] Int. Cl.⁴ .............................................. A61M 5/16
[52] U.S. Cl. ........................................................ 604/251
[58] Field of Search ................................ 604/251–255, 604/280, 284, 4, 5

[56] References Cited

U.S. PATENT DOCUMENTS

| | | | |
|---|---|---|---|
| 2,131,516 | 9/1938 | Leffert et al. | 604/251 X |
| 3,025,855 | 3/1962 | Hamilton | 604/251 |
| 3,834,386 | 9/1974 | Sisley | 604/251 |
| 3,938,539 | 2/1976 | Strouth et al. | 137/202 |
| 3,964,479 | 6/1976 | Boag et al. | 604/251 X |
| 4,143,659 | 3/1979 | Biedermann | 604/251 |
| 4,334,535 | 6/1982 | Wilson et al. | 604/251 X |

FOREIGN PATENT DOCUMENTS

| | | |
|---|---|---|
| 0082721 | 6/1983 | European Pat. Off. . |
| 2085299 | 12/1971 | France . |
| 8101793 | 9/1981 | World Int. Prop. O. . |
| 544522 | 1/1974 | Sweden . |
| 1182016 | 2/1970 | United Kingdom .................. 604/251 |
| 2021418 | 12/1979 | United Kingdom . |
| 1560660 | 2/1980 | United Kingdom . |
| 2063108 | 3/1981 | United Kingdom . |

*Primary Examiner*—Stephen C. Pellegrino
*Attorney, Agent, or Firm*—Lerner, David, Littenberg, Krumholz & Mentlik

[57] ABSTRACT

An improvement in a drip chamber for use with a tube set adapted for the extracorporeal treatment of blood and similar perishable liquids, e.g. in conjunction with dialysis, wherein the drip chamber having a lid which includes an inlet, a duct connected thereto, an outlet, a drip forming means and a sampling port structurally arranged to enable sampling of the liquid before it drips from the drip forming means. When the tube set is used as a venous branch between a dialyser and a patient, many diverse functions intended to be performed in conjunction with the venous branch can be performed in or on the drip chamber.

8 Claims, 6 Drawing Figures

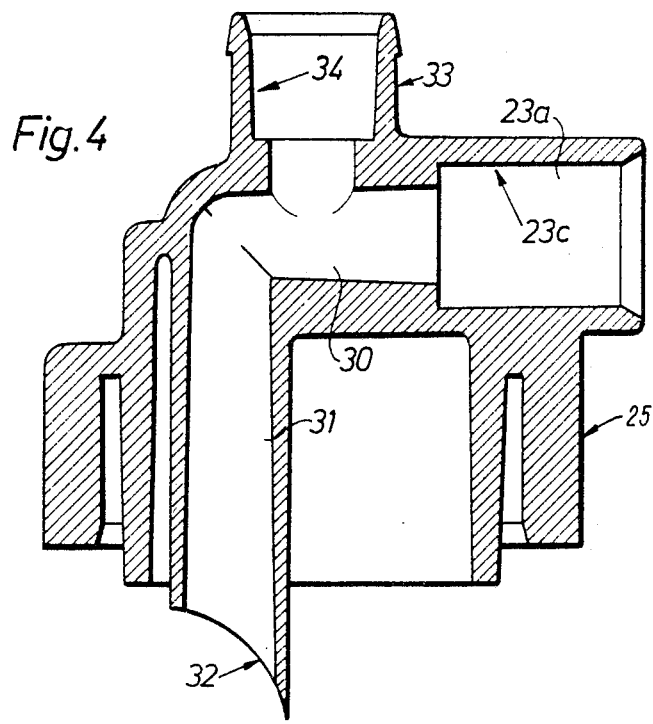
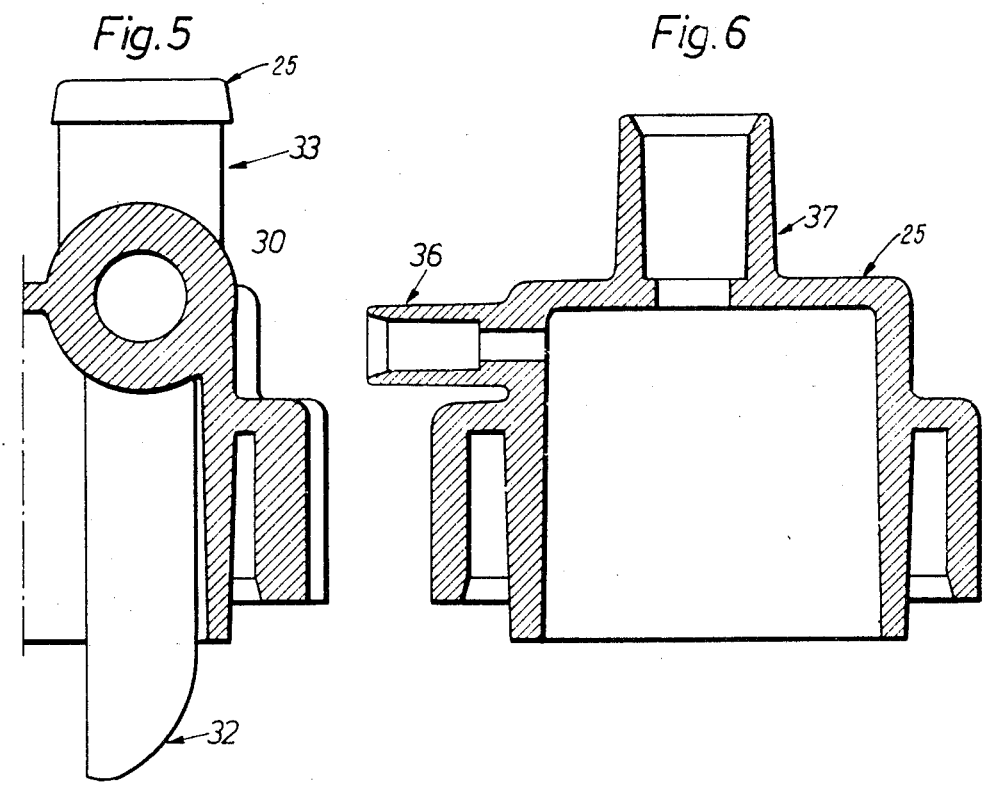

HOSE SET FOR EXTRACORPOREAL TREATMENT OF BLOOD AND SIMILAR LIQUIDS

FIELD OF THE INVENTION

The present invention relates to a tube set intended for extracorporeal treatment of blood and similar perishable liquids, e.g. by dialysis, comprising at least one drip chamber provided with an inlet and an outlet.

Such tube sets normally are made to be used only once. They are frequently divided into an arterial branch and a venous branch, the arterial branch being intended to be coupled between one of the patient's arteries and the apparatus by means of which the blood is to be treated. The venous branch is intended instead to be coupled between the blood-treating apparatus and one of the patient's veins for the return of the blood. The expression "tube set" as used herein refers first and foremost to the venous branch. However, the invention may also be applied to the arterial branch or to a tube set consisting of combinations of the arterial branch and the venous branch.

BACKGROUND OF THE INVENTION

Present tube sets normally consist of a plurality of tubes which are joined to one another by numerous branch pipes, T-pipes or other components, such as pump segments, drip chambers, pressure monitoring pads or the like, by means of which the flowing medium can be controlled and/or guided. In addition, the tube set normally includes different types of ports for the feed and/or withdrawal of liquids, e.g. for dilution and/or sampling. The various components are usually distributed at different points along the tube set.

An object of the present invention is to facilitate the assembly of the tube set on the front of a control unit, the above-mentioned components and functions associated therewith being concentrated in one or a small number of points on the front of the control unit. If possible, therefore, the tube set should consist of an unbroken tube between the front of the control unit and the patient. In this manner, the personnel performing the treatment can concentrate on the control unit and on the patient.

It is another object of the invention to facilitate sampling and other treatment of the patient.

SUMMARY OF THE INVENTION

The present invention relates to a tube set intended for extracorporeal treatment of blood and similar perishable liquids, e.g. in conjunction with dialysis, comprising at least one drip chamber with an inlet and an outlet. The invention is characterized in that the inlet and the outlet are arranged at an angle in relation to one another to thereby inhibit the tubes connected to the drip chamber from being constricted as a result of kinking. Furthermore, this inlet and outlet arrangement permits the unique positioning of ports for the supply or withdrawal of materials, e.g. for sampling and/or dilution.

The drip chamber preferably has an elongated shape with the outlet being arranged in its lower end and extending in its longitudinal direction. The inlet may be arranged in the side of a lid-like part. A sampling port is arranged directly above the inlet upstream from the point where the introduced liquid is directed downward into the drip chamber. Thus, sampling can be carried out before the liquid begins to drip and with the aid of a short suction needle.

Moreover, the drip chamber may comprise one or more ports for the withdrawal and/or supply of a material, e.g., a liquid or air. The supply or withdrawal of air is used to control the liquid level in the drip chamber. This control function may be performed in a conventional manner with the aid of a simple syringe. One or more of these ports are preferably arranged in the side in the lid-like part.

In a preferred embodiment of the invention, the drip chamber forms a part of a venous tube set for dialysis or similar treatment. In such a tube set, all of the various diverse functions to be performed in connection therewith are concentrated in or on the drip chamber, as a result of which the tube segments are completely unbroken between the dialyser or corresponding treatment apparatus and the drip chamber, as well as between the drip chamber and the patient. In this way, the personnel performing the treatment can concentrate on the control unit to which the drip chamber is normally attached and on the patient.

BRIEF DESCRIPTION OF THE DRAWINGS

For a better understanding of the present invention, reference is made to the following detailed description of an exemplary embodiment considered in conjunction with the accompanying drawings, in which:

FIG. 4 is a cross-sectional view, taken along line IV—IV of FIG. 3 and looking in the direction of the arrows, of the lid shown in FIGS. 2 and 3;

FIG. 5 is a cross-sectional view, taken along line V—V of FIG. 3 and looking in the direction of the arrows, of the lid shown in FIGS. 2 and 3; and FIG. 6 is a cross-sectional view, taken along line VI—VI of FIG. 3 and looking in the direction of the arrows, of the lid shown in FIGS. 2 and 3.

DESCRIPTION OF THE EXEMPLARY EMBODIMENT

Figure 1:
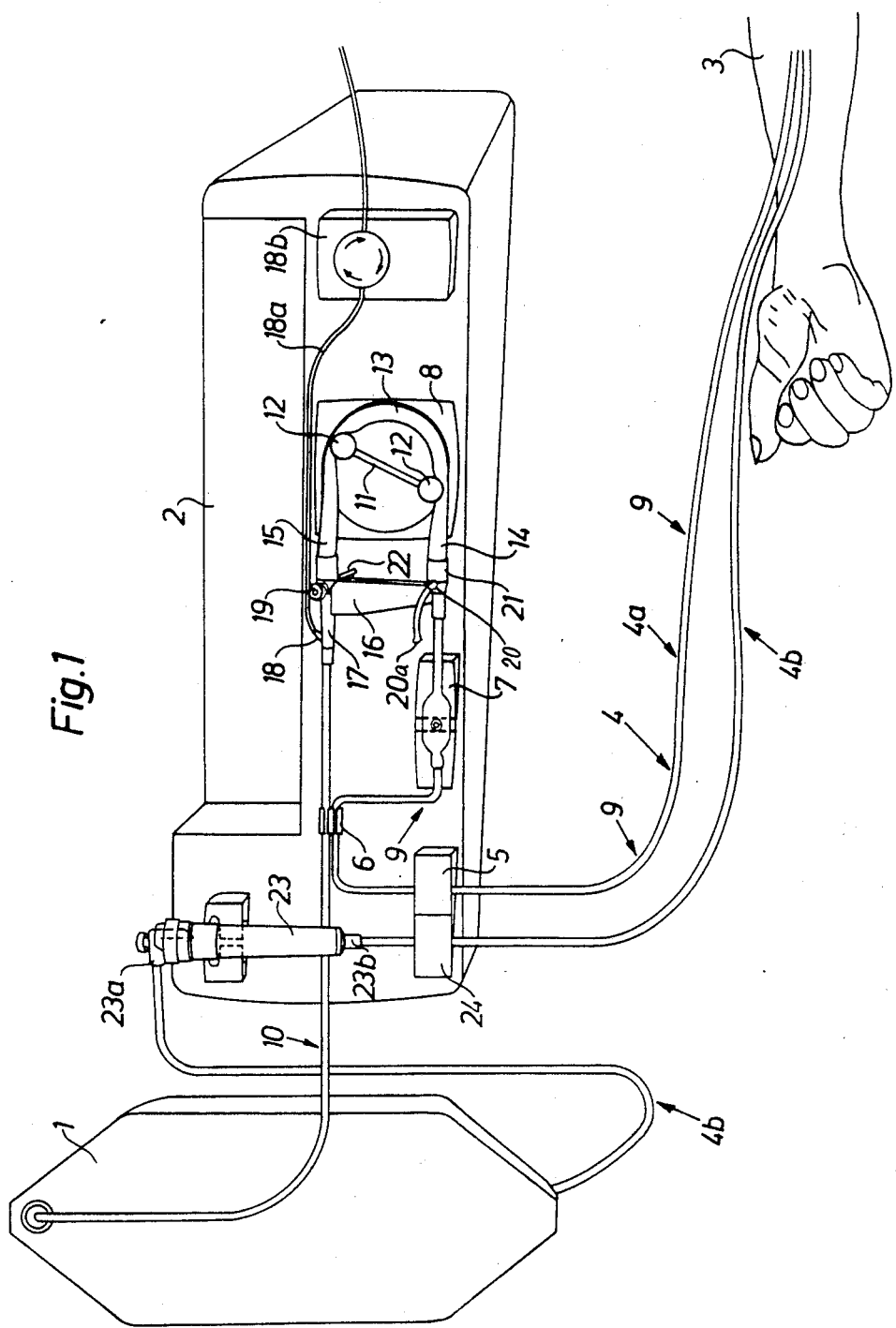
FIG. 1 is a schematic illustration of a dialyser connected to a control unit and a patient by a tube set consisting of an arterial branch and a venous branch.
Figure 2:
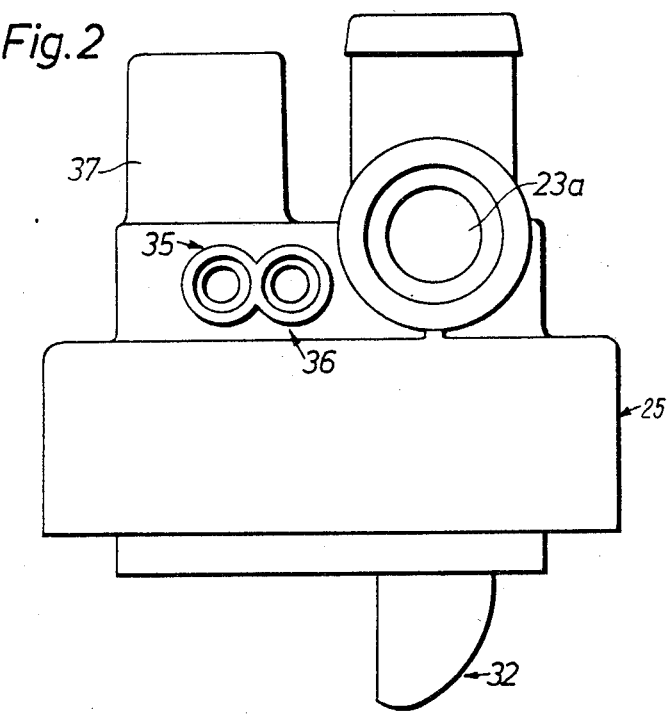
FIG. 2 is a side elevational view of a lid for a drip chamber which forms part of the tube set shown in FIG. 1.
Figure 3:
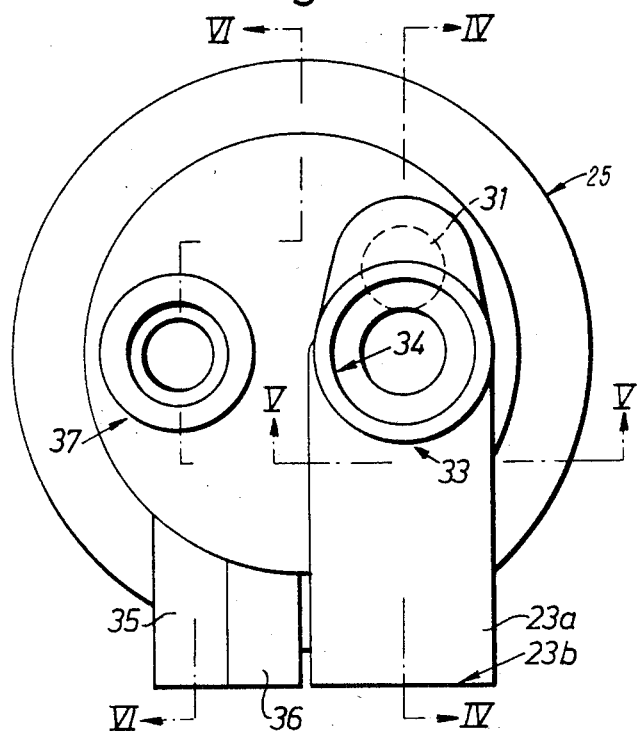
FIG. 3 is a top view of the lid shown in FIG. 2.

Referring to FIG. 1, a dialyser 1, a control unit 2 and a patient 3 are coupled together by means of a tube set designated as a whole by reference numeral 4. This tube set consists of an arterial branch 4a and a venous branch 4b. The arterial branch 4a is connected by means of an injection needle (not shown) to one of the arteries of the patient 3 and passes through a shut-off clip 5, a holder 6 and an arterial pressure monitor 7 to a pump 8 and then to the dialyser 1. The portion of the arterial branch 4a extending from the patient 3 to the suction side of the pump 8 constitutes the inlet portion of the arterial branch 4a and is designated as a whole by reference numeral 9. The portion of the arterial branch 4a between the delivery side of the pump 8 and the dialyser 1 constitutes the outlet portion of the arterial branch 4a and is designated as a whole by reference numeral 10.

The invention resides primarily in the tube set 4. Accordingly, the control unit 2 has been shown only schematically without the instruments and many other components which are normally included therein.

The pump 8 comprises, in addition to a rotor 11 with two rollers 12 securely attached to the control unit 2, a pump segment 13 incorporated in the tube set 4. The pump segment 13 has an inlet end 14 and an outlet end 15 which are rigidly connected to each other by a spacer 16.

The spacer 16 includes between the outlet end 15 of the pump segment 13 and the outlet portion 10 of the arterial branch 4a a pipe fitting 17 adapted to connect the outlet end 15 of the pump segment 13 to the outlet portion 10 of the arterial branch 4a. The fitting 17, in turn, includes an inlet 18 for the input of a reagent, e.g. heparin, and a sampling port 19 arranged upstream of the inlet 18. The distance between the inlet 18 and the outlet end 15 of the pump segment 13 and the distance between the port 19 and the outlet end 15 of the pump segment 13 are chosen so that sampling through the port 19 can take place without any risk of interference caused by the reagent introduced through the inlet 18 being sucked back towards the port 19 as a result of the suction generated in the pump segment 13. A source of heparin or the like (not shown) is connected to the inlet 18 by a tube 18a and a pump 18b. The spacer 16 is also provided between the inlet portion 9 of the arterial branch 4a and the inlet end 14 of the pump segment 13 with a pipe fitting 21. The fitting 21 includes a port 20 for the input of a liquid, e.g. priming liquid, through a tube 20a with the help of the pump 8. Finally, the spacer 16 comprises a stay 22 designed to support the spacer 16 against the front of the control unit 2 or against any other component firmly attached to the pump 8 or to the control unit 2.

From the dialyser 1, venous branch 4b of the tube set 4 passes through a drip chamber 23, which has an inlet 23a and an outlet 23b, and a shut-off clip 24 back to the patient 3. What follows is a more detailed description of the drip chamber 23.

Referring now to FIGS. 2-6, the drip chamber 23 has a lid 25. The inlet 23a is arranged in the side of the lid 25 and extends generally horizontally in relation to the drip chamber 23, which is designed for vertical installation. The inlet 23a is provided with a seat 23c adapted to receive the portion of the venous branch 4b arranged between the dialyser 1 and the drip chamber 23. A horizontal duct 30 extends from the inlet 23a to a vertical duct 31, the lower part of which is gently rounded so as to produce a suitable drip formation. A sampling port 33 is arranged above the horizontal duct 30. The port 33 communicates with the horizontal duct 30 at a point upstream from the intersection of the horizontal duct 30 and the vertical duct 31. A seat 34 in the port 33 is adapted to hold a rubber stopper or the like through which a syringe may be inserted.

To allow the concentrating of further functions on the drip chamber 23, the lid 25 is provided with ports 35, 36 and 37. The port 35, for example, may be used to control the liquid level within the drip chamber 23 through the supply or withdrawal of air with the aid of an ordinary syringe. The port 36 may be connected to a pressure gauge for monitoring the pressure in the venous line 4b. Finally, the port 37 can be adapted for the infusion of a dilution liquid, e.g., makeup liquid, in haemofiltration. Thus, all of the functions which are customary in a venous tube set are concentrated on the drip chamber 23, more particularly, on its lid 25.

It will be understood that the embodiment described above is only exemplary and that a person skilled in the art may make many variations and modifications without departing from the spirit and scope of the present invention. For instance, the different ports mentioned above may be arranged so as to fulfill functions other than those mentioned by way of example. Furthermore, the tube set can be provided, of course, with additional components so as to perform other functions. Such additional components, such as the arterial branch of the tube set with its unique spacer, are described in greater deail in U.S. patent application Ser. No. 530,081, filed concurrently herewith and corresponding to Swedish Patent Application No. 8205159-0, which applications are incorporated herein by reference. All such modifications and variations are intended to be included within the scope of the invention as defined in the appended claims.

We claim:

1. In a drip chamber for insertion in a venous tube set adapted for use in connection with the extracorporeal treatment of blood or other perishable liquids, which drip chamber includes a body having an upper end and a lower end, a generally vertical outlet arranged in said lower end of said body, and a lid attached to said upper end of said body, the improvement wherein said lid includes an interior, a generally horizontal inlet arranged in a side of said lid, a generally horizontal duct having an outer end in communication with said inlet and an inner end positioned in said interior of said lid, drip forming means depending generally vertically from said inner end of said duct for forming drips out of liquid flowing through said duct from said outer end thereof to said inner end thereof, and a sampling port communicating with said duct between said inner and outer ends thereof, whereby liquid flowing through said duct can be sampled before it drips from said drip forming means.

2. The improved drip chamber according to claim 1, wherein said lid further includes a plurality of additional ports, each of said additional ports being sized and shaped so as to permit material to be supplied to or withdrawn from said drip chamber, whereby various diverse functions to be performed in connection with said venous tube set can be performed through said additional ports.

3. The improved drip chamber according to claim 1, wherein said drip chamber has an elongated shape and said outlet extends in a direction generally parallel to a longitudinal axis of said drip chamber.

4. The improved drip chamber according to claim 1, wherein said inlet is arranged at approximately a right angle relative to said outlet.

5. In a venous tube set adapted to be used in connection with the extracorporeal treatment of blood or other perishable liquids, which tube set includes a drip chamber arranged between blood or other similar liquid treating apparatus and a patient and having a body provided with an upper end and a lower end, a generally vertical outlet arranged in said lower end of said body, and a lid attached to said upper end of said body, the improvement wherein said lid includes an interior, a generally horizontal inlet arranged in a side of said lid, a generally horizontal duct having an outer end in communication with said inlet and an inner end positioned in said interior of said lid, drip forming means depending generally vertically from said inner end of said duct for forming drips out of liquid flowing through said duct from said outer end thereof to said inner end thereof, a sampling port communicating with said duct between said inner and outer ends thereof, whereby liquid flowing through said duct can be sampled before it drips from said drip forming means, and a plurality of additional ports, each of said additional ports being sized and shaped so as to permit material to be supplied to or withdrawn from said drip chamber through said lid, whereby various diverse functions to be performed in connection with said venous tube set can be performed through said additional ports.

6. The improved venous tube set according to claim 5, wherein at least one of said additional ports is arranged in said side of said lid.

7. The improved venous tube set according to claim 5, wherein said drip chamber has an elongated shape and said outlet extends in a direction generally parallel to a longitudinal axis of said drip chamber.

8. The improved venous tube set according to claim 5, wherein said inlet is arranged approximately at a right angle relative to said outlet.

* * * * *